United States Patent
Fleischer et al.

(10) Patent No.: US 9,234,871 B2
(45) Date of Patent: Jan. 12, 2016

(54) GAS SENSOR

(75) Inventors: Maximilian Fleischer, Hoehenkirchen (DE); Roland Pohle, Herdweg (DE); Kerstin Wiesner, Putzbrunn (DE); Oliver Von Sicard, Munich (DE)

(73) Assignee: Siemens Aktiengesellschaft, Munich (DE)

( * ) Notice: Subject to any disclaimer, the term of this patent is extended or adjusted under 35 U.S.C. 154(b) by 97 days.

(21) Appl. No.: 13/464,604

(22) Filed: May 4, 2012

(65) Prior Publication Data

US 2012/0282142 A1    Nov. 8, 2012

(30) Foreign Application Priority Data

May 6, 2011    (DE) .......................... 10 2011 075 396

(51) Int. Cl.
  *G01N 27/00*     (2006.01)
  *H01L 27/28*     (2006.01)
  *H01L 51/00*     (2006.01)
  *G01N 27/414*    (2006.01)

(52) U.S. Cl.
  CPC ................................. *G01N 27/4143* (2013.01)

(58) Field of Classification Search
  CPC .... G01N 27/00; G01N 27/4143; H01L 27/28; H01L 51/00
  USPC ........... 422/50, 83, 98; 73/23.2, 31.05, 31.06; 438/48, 49; 257/213, 252, 253
  See application file for complete search history.

(56) References Cited

U.S. PATENT DOCUMENTS

2007/0235773 A1* 10/2007 Eisele et al. .................. 257/253
2008/0237654 A1* 10/2008 Lehmann et al. ............. 257/253

FOREIGN PATENT DOCUMENTS

| DE | 102004019639 | 11/2005 |
|----|--------------|---------|
| DE | 10 2005 010 032 A1 | 9/2006 |
| WO | 2010/078337 | 7/2010 |
| WO | 2011/053820 | 5/2011 |

OTHER PUBLICATIONS

Achmann et al., Metal-organic frameworks for sensing applications in the gas phase, Sensors 2009, 9, 1574-1589.*
Joo et al., Chemical sensors with integrated electronics, Chem. Rev. 2008, 108, 638-651.*
Fleischer, Maximilian, et al. "Detection of volatile compounds correlated to human diseases through breath analysis with chemical sensors." Sensors and Actuators B: Chemical 83.1 (2002): 245-249.*
Biemmi, Enrica, et al. "Direct growth of Cu< sub> 3</sub>(BTC)< sub> 2</sub>(H< sub> 2</sub> O)< sub> 3</sub>•< i> x</i> H< sub> 2</sub> O thin films on modified QCM-gold electrodes—Water sorption isotherms." Microporous and Mesoporous Materials 114.1 (2008): 380-386.*
Sabine Achmann et al., "Metal-Organic Frameworks for Sensing Applications in the Gas Phase", Sensors, vol. 9, No. 3, Jan. 2009, pp. 1574-1589.

(Continued)

*Primary Examiner* — Lyle Alexander
*Assistant Examiner* — Robert Eom
(74) *Attorney, Agent, or Firm* — Staas & Halsey LLP

(57) ABSTRACT

Volatile organic compounds or oxidizing gases are detected when the work function of a metal-organic framework is measured to produce a sensor signal.

12 Claims, 1 Drawing Sheet

(56) References Cited

OTHER PUBLICATIONS

Mark D. Allendorf et al., "Stress-Induced Chemical Detection Using Flexible Metal-Organic Frameworks". Journal of American Chemical Society, vol. 130, No. 44, Nov. 2008, pp. 14404-14405.

European Office Action issued Jul. 27, 2012 in corresponding European Patent Application No. 12163573.4.
German Office Action dated Apr. 25, 2012 issued in corresponding German Patent Application No. 102011075396.6.
Ralf Moos et al., "Solid State Gas Sensor Research in Germany—a Status Report" Sensors, Jun. 2009, pp. 4323-4365.

* cited by examiner

GAS SENSOR

CROSS REFERENCE TO RELATED APPLICATIONS

This application is based on and hereby claims priority to German Application No. 10 2011 075 396.6 filed on May 6, 2011, the contents of which are hereby incorporated by reference.

BACKGROUND

The detection or measurement of volatile organic compounds (VOC) is of great interest for a number of applications. Examples are assessment of the air quality in rooms, the energy-efficient control of air conditioning plants, medical diagnostics, safety technology such as the detection of explosives or the monitoring of purified air. A problem with volatile organic compounds is that they come in a very great molecular variety. Important representatives are, for example, aldehydes, alcohols, amines, carboxylic acids, esters, ketones, hydrocarbons, terpenes, thiols, etc. This variety makes it difficult to realize a sensor which gives a sufficiently high sensor signal for a major part of the volatile organic compounds. Odors are often made up of a plurality of compounds which are also frequently present in very small amounts. Volatile organic compounds generally have such a low odor threshold that concentrations which are clearly perceptible to human beings are at the same time very difficult to detect technically.

SUMMARY

Described below is an apparatus for the detection of at least one volatile organic compound or at least one oxidizing gas, by which even small amounts of the volatile organic compound or of the oxidizing gas can be measured.

The apparatus described below uses a measuring material whose electronic work function is changed on interaction with a volatile organic compound or an oxidizing gas. The measuring material includes a material selected from the group consisting of metal-organic frameworks (MOFs). The apparatus measures changes in the electronic work function of the measuring material.

The inventors recognized that the particular characteristic of metal-organic frameworks is a large hollow space in the middle of a unit cell of the metal-organic framework. This hollow space makes the use of metal-organic frameworks in sensors for gases possible. Here, the large internal surface area (up to more than 4000 m$^2$/g) is important and a great advantage. This large internal surface area is available for interaction with gases. Furthermore, a high selectivity for particular substances can advantageously be achieved by fixing the size of the pores or of the hollow space. This can in turn be controlled via the size of the organic ligands. Matching to a gas to be detected can be carried out in this way.

It has surprisingly been found to be possible to use metal-organic frameworks in gas sensors. The position of the hollow spaces in the middle of the unit cells of the metal-organic framework is at a large distance, on the scale of electronic interaction, from measuring a change in the work function. In other words, the interaction with the gas at the interior surfaces of the metal-organic framework is at a comparatively large distance from the surface of the measuring material. A measurable change in the work function as a result of influences of gas was therefore not to be expected. Nevertheless, experiments have shown that gas sensors using metal-organic frameworks give good results for volatile organic compounds.

In an advantageous embodiment, the apparatus includes a heater device, for example a heating meander structure. This can serve firstly to bring the metal-organic framework to a required operating temperature. Secondly, it is also possible, in the case of a measurement at room temperature, to reset the sensor by heating if some of the chemical reactions are irreversible or reversible only with difficulty at room temperature.

In the process of producing an apparatus for measuring at least one volatile organic compound or at least one oxidizing gas, a measuring material whose electronic work function is changed on interaction with the volatile organic compound or the oxidizing gas is applied to a support, in particular to a silicon substrate. The measuring material may include a material from the group consisting of metal-organic frameworks. Furthermore, changes in the electronic work function of the measuring material are measured. Here, the measuring material is applied as a layer using an organic binder which is not gas-sensitive, in particular ethylcellulose. The organic binder remains in the layer and ensures satisfactory adhesion of the layer to the support. The layer can, for example, be applied by known screen printing or spin coating processes.

BRIEF DESCRIPTION OF THE DRAWINGS

These and other aspects and advantages will become more apparent and more readily appreciated from the following description of the exemplary embodiments, taken in conjunction with the accompanying drawings of which.

DETAILED DESCRIPTION OF THE PREFERRED EMBODIMENT

Figure 1:
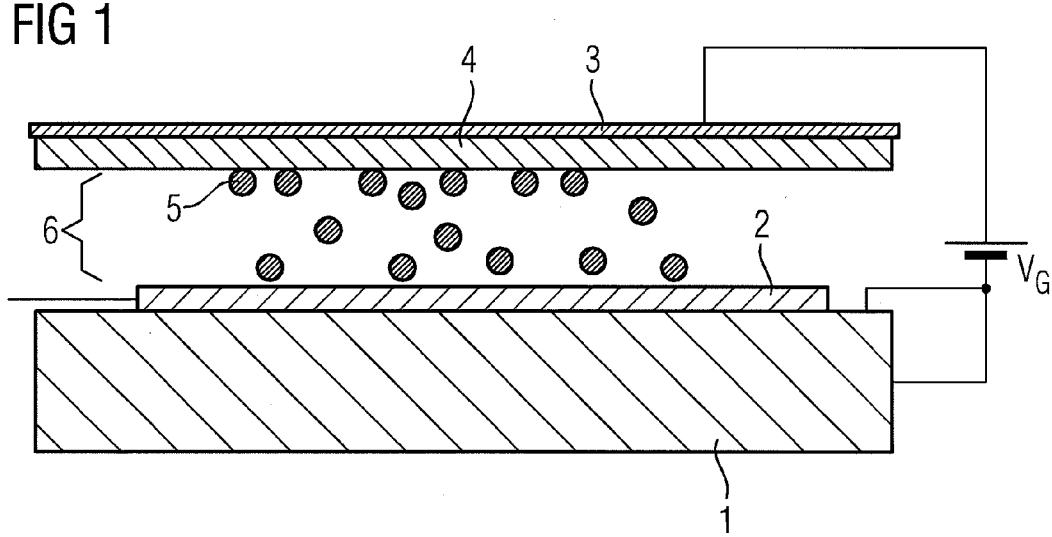
FIG. 1 is a schematic cross section of a gas sensor having a sensitive layer with a metal-organic framework and FIG. 2 is a graph of a measurement result of the gas sensor.

Reference will now be made in detail to the preferred embodiments, examples of which are illustrated in the accompanying drawings, wherein like reference numerals refer to like elements throughout.

FIG. 1 shows, in highly schematic form, an illustrative structure of a sensor. A substrate 1, for example a silicon substrate, bears a field effect transistor structure which has a drain electrode and a source electrode and is not shown in more detail. Both are covered by a passivation layer 2. Above the passivation layer 2 and separated by an air gap 6, there is a support 3 having a gas-sensitive layer 4. The gas-sensitive layer 4 has a metal-organic framework, in this example a porous $Cu_3BTC_2$ metal-organic framework.

Sensors can also be produced using, for example, the metal-organic frameworks Basolite F300 iron benzene-1,3,5-tricarboxylate and C300 copper benzene-1,3,5-tricarboxylate available from BASF. Basolite A100 aluminum terephthalate and Basolite Z1200 2-methylimidazolezinc can also be used.

Gas molecules 5 permeate into the air gap 6. Here, they become incorporated in the gas-sensitive layer 4, i.e. the metal-organic framework, and change the work function of the latter. This change is measured by the field effect transistor structure. For example, the flow of current through the field effect transistor structure is monitored and changes in the current are recorded as sensor signal. A further possibility, which is indicated in FIG. 1, is electrical connection of the gas-sensitive layer 4 to the substrate 1. A voltage source located in-between regulates the shift current which is generated in the case of changes in the work function to 0 and the voltage necessary for this is used as sensor signal.

Figure 2:
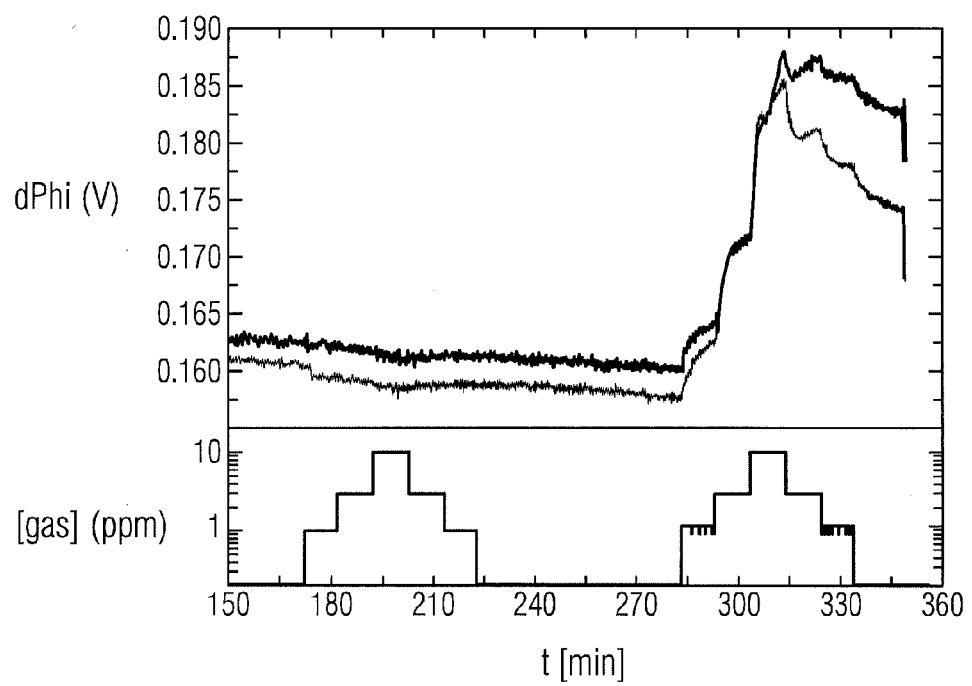

FIG. 2 shows two measurement curves of the sensor described by way of example. Here, the change in the work function is plotted as a function of time. In addition, the concentration in which the gases toluene and pentanal were fed to the sensor is shown in the lower part of the graph. Both measurement curves show no appreciable deflection in the region of the addition of toluene which was used in a maximum concentration of 10 ppm. However, the addition of likewise not more than 10 ppm of pentanal leads to a very distinct sensor deflection and sensor signal.

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in *Superguide* v. *DIRECTV,* 358 F3d 870, 69 USPQ2d 1865 (Fed. Cir. 2004).

What is claimed is:

1. An apparatus for measuring at least one of a volatile organic compound and an oxidizing gas, comprising:
    a measuring material, at least a portion being selected from the group consisting of metal-organic frameworks, having an electronic work function changed on interaction with the at least one of the volatile organic compound and the oxidizing gas; and
    a field effect transistor measuring structure, including a drain and a source covered by a passivation layer, measuring changes in the electronic work function of the measuring material,
    wherein the measuring material is provided in a region of a gate of the field effect transistor measuring structure and the measuring material includes a $C_9H_3FeO_6$ metal-organic framework.

2. The apparatus as claimed in claim 1, wherein the gate of the field effect transistor measuring structure is separated by an air gap from a remainder of the field effect transistor measuring structure.

3. The apparatus as claimed in claim 2, further comprising a heater device heating the metal-organic framework.

4. The apparatus as claimed in claim 1, further comprising a heater device heating the metal-organic framework.

5. The apparatus as claimed in claim 1, wherein the measuring material is provided in an air gap separating a gate of the field effect transistor measuring structure from a drain and a source of the field effect transistor measuring structure.

6. The apparatus as claimed in claim 5, further comprising a heater device heating the metal-organic framework.

7. An apparatus for measuring at least one of a volatile organic compound and an oxidizing gas, comprising:
    a measuring material, at least a portion being selected from the group consisting of metal-organic frameworks, having an electronic work function changed on interaction with the at least one of the volatile organic compound and the oxidizing gas; and
    a field effect transistor measuring structure, including a drain and a source covered by a passivation layer, measuring changes in the electronic work function of the measuring material,
    wherein the measuring material is provided in a region of a gate of the field effect transistor measuring structure and the measuring material includes a $C_8H_{12}N_4Zn$ metal-organic framework.

8. The apparatus as claimed in claim 7, wherein the gate of the field effect transistor measuring structure is separated by an air gap from a remainder of the field effect transistor measuring structure.

9. The apparatus as claimed in claim 8, further comprising a heater device heating the metal-organic framework.

10. The apparatus as claimed in claim 7, further comprising a heater device heating the metal-organic framework.

11. The apparatus as claimed in claim 7, wherein the measuring material is provided in an air gap separating a gate of the field effect transistor measuring structure from a drain and a source of the field effect transistor measuring structure.

12. The apparatus as claimed in claim 11, further comprising a heater device heating the metal-organic framework.

* * * * *